United States Patent [19]
Patton et al.

[11] Patent Number: 5,895,871
[45] Date of Patent: Apr. 20, 1999

[54] FINGER CONTROLLED INSPECTION APPARATUS

[75] Inventors: Thadd Clark Patton, Cincinnati, Ohio; Robert John Filkins, Fonda, N.Y.; James Paul Fulton, Ballston Lake, N.Y.; Kristina Helena Valborg Hedengren, Schenectady, N.Y.; John David Young, Rexford, N.Y.

[73] Assignee: General Electric Company, Schenectady, N.Y.

[21] Appl. No.: 08/900,343

[22] Filed: Jul. 25, 1997

[51] Int. Cl.$^6$ ........................ A61B 5/00
[52] U.S. Cl. ........................ 73/866.5
[58] Field of Search .............. 73/866.5, 598, 73/597, 629, 661, 644, 865.7, 864.71, 862.68, 862.69; 324/228–231, 234, 239; 374/208, 209

[56] References Cited

U.S. PATENT DOCUMENTS

| | | |
|---|---|---|
| 4,144,877 | 3/1979 | Frei et al. |
| 5,012,817 | 5/1991 | Zeilinski et al. |
| 5,230,921 | 7/1993 | Waltonen et al. |
| 5,572,995 | 11/1996 | Rohrberg |

Primary Examiner—Robert Raevis
Attorney, Agent, or Firm—David C. Goldman; Marvin Snyder

[57] ABSTRACT

An exemplary inspection apparatus for inspecting an article comprises a flexible sensor for sensing a characteristic of the article, which sensor conforms to a surface of the article, a finger cover which fits over a finger of a user, and an attachment device for removably attaching the sensor to the finger cover. The apparatus allows the user to traverse the sensor over a large range of smoothly varying concave or convex inspection surfaces, for example, while providing the user with direct control of the sensor.

14 Claims, 5 Drawing Sheets

FINGER CONTROLLED INSPECTION APPARATUS

The government may have certain rights in this invention pursuant to contract no. FAA93-G-08-029 awarded by the Federal Aviation Administration.

BACKGROUND

1. Field of the Invention

The present invention relates generally to nondestructive testing, and more particularly to a finger-tip probe for nondestructive testing which comprises a flexible sensor.

2. Description of the Related Art

In the field of nondestructive testing (NDT), ultrasound and eddy current techniques are commonly used to characterize material properties and detect flaws in parts under inspection. Ultrasound, which is typically used for volumetric inspection, involves the generation and detection of ultrasonic waves in a part with an ultrasonic transducer. Eddy current methods, which are commonly used to inspect the surface of a part, involve the electromagnetic induction of eddy currents within the part using a changing magnetic field, and the detection of eddy current effects to determine part characteristics or flaws.

Performance of many NDT systems can be improved by placing the sensors in direct contact with the part under inspection, because commonly the inspection sensitivity is directly related to the placement, proximity, and coupling of the sensors to the surface of the part. The accuracy of NDT techniques may thus be influenced by geometrical constraints of the probe which houses the sensor and the exterior boundary conditions of the part. The exterior boundary conditions may include, for example, surface curvature, which may introduce limitations to the performance of the inspection system. Other exterior boundary conditions include surface roughness, external coatings, support structures, corrosion, and fasteners.

To provide flexibility in inspecting parts having a surface curvature, known systems utilize a flexible eddy current coil or ultrasonic sensor integrated into a multilayer flexible polymer film. This arrangement, which enables the sensors to be efficiently coupled to a curved part, eliminates the need to maintain a large inventory of probes tailored to fit individual geometries and curvature conditions of various parts.

Another factor which influences the sensitivity of the sensor is the pressure with which the sensor is applied to the part. A uniform pressure properly couples the interactions between the sensor and the part under inspection. Uniform pressure reduces variations in signal response to factors not directly related to the detection of material flaws or material properties. To achieve a uniform pressure at different inspection sites, a known solution utilizes compressed gas at a controlled pressure applied against the back of a flexible eddy-current sensing coil array. The eddy current sensing coil array is disposed in an eddy current probe which is under the control of a multi-axis mechanical control system which precisely manipulates the probe over the part. The complexity of such a system, however, may limit its usefulness due to cost considerations. The size of the system may also limit its accessibility to remote parts.

Hand held probes are known which provide NDT data without the substantial cost associated with a multi-axis control system. One known hand held probe includes a mechanism for applying a uniform pressure to the part surface, which pressure is decoupled from the pressure the operator uses to apply the probe against the part. Hand held probes, however, typically include a supporting structure which limits the accessibility of the probe to remote regions of a part and which makes the probe somewhat cumbersome to use.

It would be desirable, therefore, to have an inspection apparatus which was able to reach relatively inaccessible regions of a part and apply a uniform pressure to the surface of the part at a low cost.

SUMMARY

An exemplary inspection apparatus for inspecting an article comprises a flexible sensor for sensing a characteristic of the article, which sensor conforms to a surface of the article, a finger cover which fits over a finger of a user, and an attachment device for removably attaching the sensor to the finger cover.

The finger controlled inspection apparatus provides a simple and inexpensive means of manually applying a flexible sensor with uniform pressure to the part under inspection. The apparatus allows the sensor to be traversed over a large range of smoothly varying concave or convex inspection surfaces, for example, while providing the user with direct control of the sensor.

BRIEF DESCRIPTION OF THE DRAWINGS

Other features and advantages of the invention will be more readily understood upon reading the following detailed description, in conjunction with the drawings, in which.

DETAILED DESCRIPTION OF THE PREFERRED EMBODIMENTS

Figure 1:
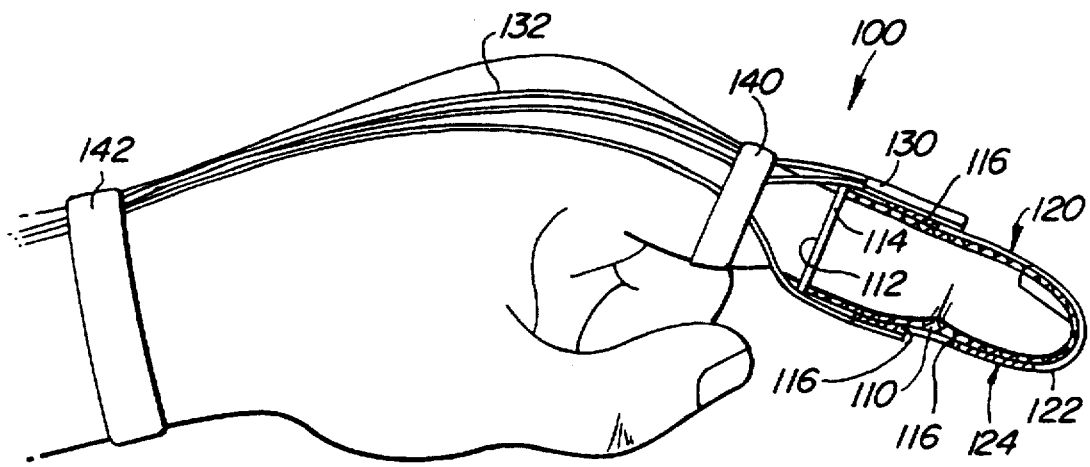
FIG. 1 is a side view of an inspection apparatus according to an exemplary embodiment of the invention.
Figure 2:
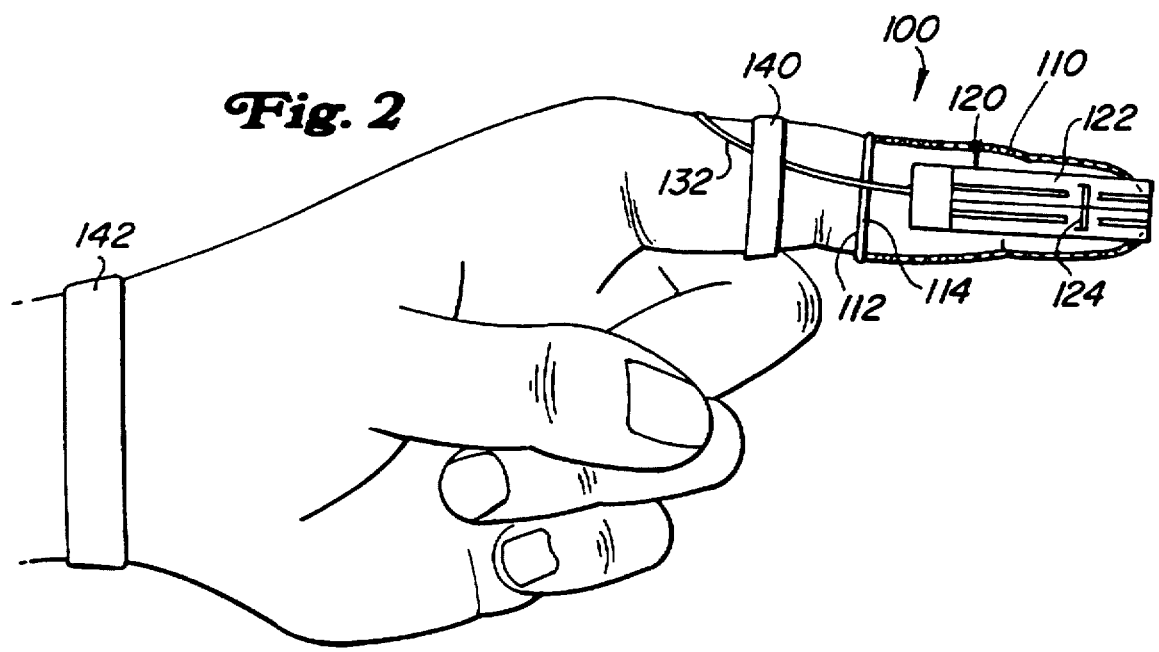
FIG. 2 is a bottom view of the inspection apparatus of FIG. 1.
Figure 6:
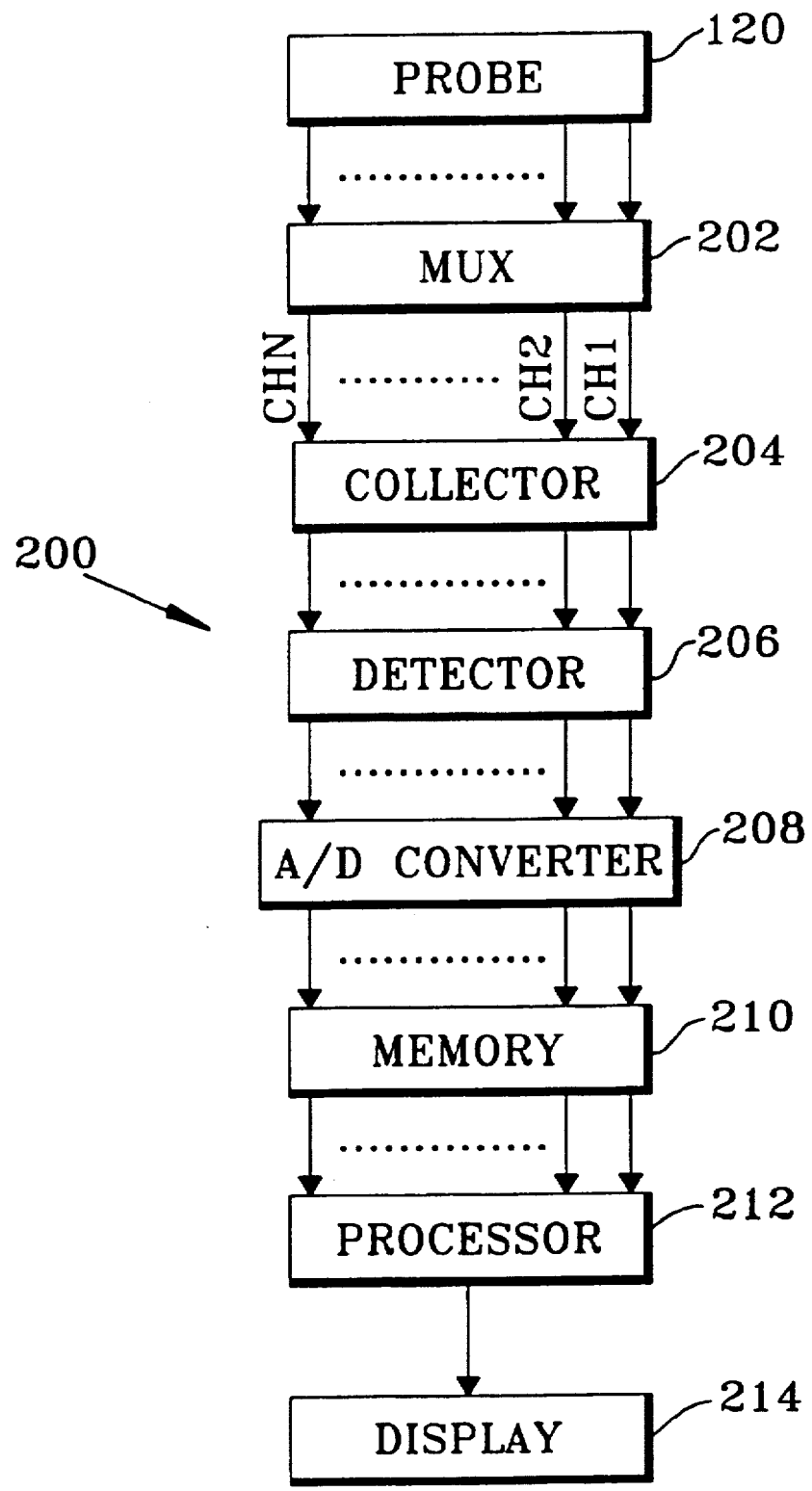
FIG. 6 is an electronic processing system for processing the data generated with the probe.

Referring to FIGS. 1 and 2, an exemplary inspection apparatus 100 is shown which includes a probe 120 having at least one sensor 124 for sensing material properties and flaws of a part under inspection. The sensor of the probe is supported in a flexible film and is connected with electrical wires to an electronic processing system (FIG. 6). The probe is secured to the user's finger with a finger cover 110, which gives the user a large degree of control over the manipulation of the probe on the part being inspected. The electronic processing system processes the data obtained with the probe to, for example, detect flaws in, characterize the material properties of, or characterize flaws in the part being inspected. The electronic processing system may, for example, generate an audio or visual signal representative of eddy currents induced in the part, or generate an image of the part, based on the data obtained with the probe.

The probe 120 comprises at least one sensor such as an eddy current sensor 124 (FIG. 2), an ultrasonic sensor 124' (FIG. 7), or both. The sensors are preferably flexible so that they can conform to the surface of the part being inspected when pressure is applied. The sensor or sensors are supported in a flexible film 122, which may comprise a polymer, for example. The flexible sensor or sensors integrated in the flexible film 122 can conform to the surface of the part.

According to one embodiment, as shown in FIG. 2, the probe 120 includes an eddy current sensor 124. The eddy current sensor 124 includes a drive coil which generates an alternating magnetic field when an alternating current is passed through it. The magnetic field, in turn, generates eddy currents in the part under inspection through electromagnetic induction. The eddy current sensor 124 includes a sense coil for sensing the eddy currents induced in the part. The flow of the eddy currents is used to characterize and detect material properties and flaws in the part. For example, the eddy current flow is affected by cracks, since an open crack causes eddy currents to detour around it, which changes the electrical impedance of the sensor over that region of the part. The eddy current flow is also influenced by factors such as hardness, chemical composition, and thickness, which affect the electrical properties of the part. Detection of eddy current effects, through the use of magnitude and phase measurements with appropriate impedance plane instruments, can therefore be used to characterize properties and detect flaws in the part.

Figure 5:
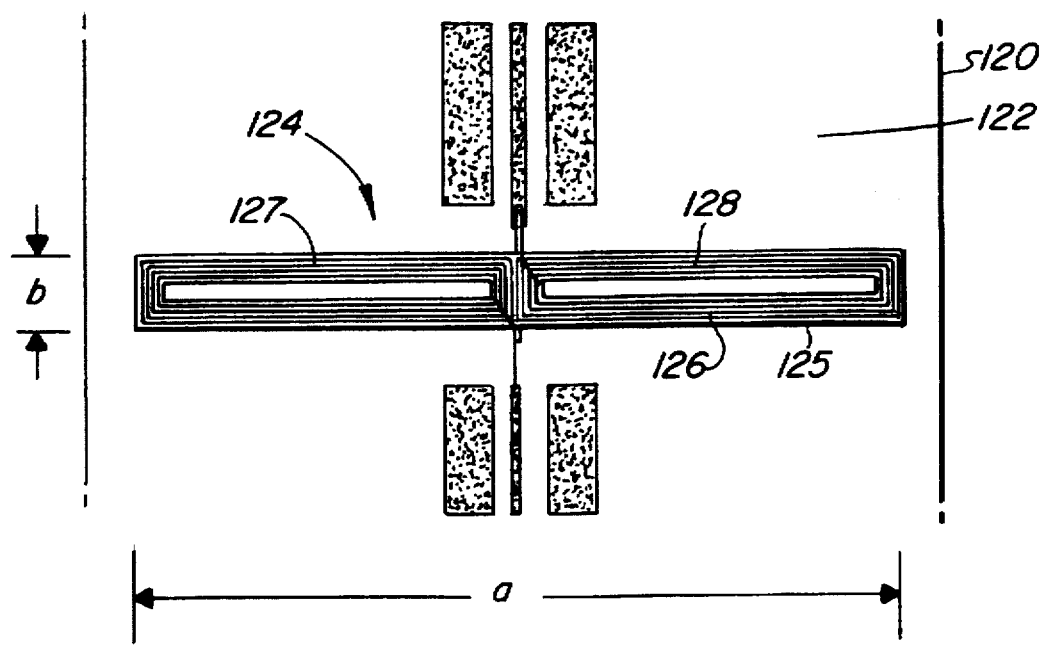
FIG. 5 is an enlarged view of the eddy current coil of FIG. 2.

FIG. 5 is an enlarged view of the sensor 124 of FIG. 2, which illustrates an exemplary eddy current coil arrangement. In FIG. 5, the sensor 124 includes a separate drive coil 125 and sense coil 126. The drive coil can be a single or multiple loop coil disposed along the perimeter of the coil arrangement. The sense coil 126 typically includes multiple loops, and is commonly a subtractive or "differential" coil. The drive and sense coils can occupy different layers of a multilayer probe. The drive and sense coils may be embedded in a flexible polymer film such as Kapton™, a polyimide available from E. I. DuPont de Nemours Company to form the probe 120. The construction of the probe is described in more detail in commonly-owned U.S. Pat. No. 5,389,876, which is hereby incorporated by reference.

As shown in FIG. 5, the differential sense coil 126 includes two sub-coils 127, 128, which are wound in opposite directions. The differential sense coil 126 generates a signal representative of the difference between a first eddy current sensed by the first sub-coil 127 and a second eddy current sensed by the second sub-coil 128. Thus, when a crack is located below only one of the two sub-coils, the differential signal will be large. When the eddy current effects detected by the two sub-coils are of about the same Magnitude, the differential signal will be small or zero. The differential sense coil also reduces the inspection dependence to pressure, contact, temperature, and local changes in conductivity over the part under inspection.

For a typical application, the length "a" (FIG. 5) of the sensor 124 is about ½ inch, and the width "b" is about ¹⁄₁₆ inch. These dimensions, according to an exemplary embodiment of the invention, are used to accommodate various considerations for detection efficacy. First, the width of the sense coil should be small enough to precisely locate small cracks. Second, the length of the sense coil should be large enough to expedite the inspection of large areas. Third, the area of the sense coil should be large enough to generate a suitably large voltage signal. Thus, the width of the sense coil is relatively small, while the length is relatively large. The number of turns in the sense coil can also be increased to provide a greater signal strength.

Although the exemplary probe 120 shown in FIG. 2 includes a single sensor 124, multiple sensors may be included on the probe 120. For example, first and second eddy current sensors may be provided which are staggered with respect to their lengths to eliminate the possibility that a crack will go undetected because it lies perpendicularly between the two sub-coils 127, 128 on a single sensor 124. Other sensor arrangements may be implemented, for example an "absolute" sensor which includes a single coil acting as both the drive coil and the sense coil. An "absolute" sensor may be implemented to measure the absolute magnitude of eddy current effects, which magnitude may be subsequently compared to a reference signal to determine a part thickness, for example.

Various combinations of single and multiple eddy current coil arrangements are possible with the flexible film arrangement according to exemplary embodiments of the invention. For example, the eddy current coils can be connected in an array configuration with single or multiple sense and drive lines using multichannel and multiplexing systems. Single eddy current coil configurations can be used with conventional single channel eddy scope instruments to cover small or large inspection areas. Large inspection regions can be accommodated by a single large coil or through the use of several small coil arrangements connected in series or in parallel. The electronic processing system (FIG. 6) may accordingly have single or multiple channels depending on the number of sensors on the probe 120.

Figure 7:
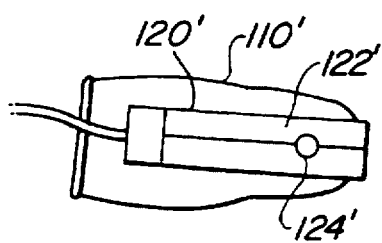
FIG. 7 is an exemplary embodiment of a probe which includes an ultrasonic transducer.

According to another embodiment of the invention, as shown in FIG. 7, the probe 120' includes an ultrasonic transducer 124', which typically comprises a piezoelectric element. The ultrasonic transducer may comprise, for example, a polyvinylidene fluoride (PVDF) piezoelectric element which is imbedded in a flexible polymer film 122' to form the probe 120'. The center frequency of the ultrasonic transducer can be controlled by the thickness of the PVDF film. The bandwidth of the ultrasonic transducer can be controlled by a combination of the damping characteristics of the pad of the user's finger and other thin damping materials coupled to the transducer, such as rubber or epoxy. A typical piezoelectric element may comprise a 25 micron thick disc of PVDF having a diameter of about ¼ inch imbedded in a flexible polymer film, serving as both a transmitter and a receiver of ultrasonic signals.

The piezoelectric element of the ultrasonic transducer vibrates at an ultrasonic frequency, e.g. from 1–10 mHz, when an appropriate voltage is applied to generate ultrasonic waves in the part. The ultrasonic waves propagate through the part and are reflected at interfaces or flaws in the part to produce reflected waves. The piezoelectric element also receives the reflected waves and generates electric signals representative of the reflected waveforms. The electric signals contain information on the characteristics or flaws of the part, which information is processed by the electronic processing system to characterize or image the part.

According to another embodiment of the invention, the ultrasonic sensor can comprise a plurality of flexible ultrasonic transducers in the form of a flexible film of piezoelectric elements. The piezoelectric elements can be connected in an array configuration with single or multiple sense and drive lines using multichannel and multiplexing systems.

The number, size, shape, orientation, and position of the eddy current elements and the piezoelectric elements is not limited to the implementations shown in FIGS. 2 and 7, and can vary. The probe 120 may include, for example, both flexible eddy current elements and piezoelectric elements, as described, for example, in commonly-owned U.S. patent application Ser. No. 08/880,322, filed Jun. 23, 1997 by Patton et al., entitled "Probe and Method for Inspecting an Object", which is hereby incorporated by reference. The probe may also include a thermocouple sensor which is appropriately thermally shielded from the user's body.

As shown in FIG. 1, the inspection apparatus 100 may include a signal preamplifier 130 which is electrically connected to the eddy current sensor and/or ultrasonic transducer. The location of the preamplifier 130 adjacent to the probe 120 improves the signal-to-noise ratio of the inspection apparatus 100 and thus improves characterization and flaw detection. Transformer coupling of the sensed signals can also be performed with a transformer coupled to the probe 120, which improves the signal to noise ratio, or at the connection to the electronic processing system, for example. The transformer amplifies the voltage signal by the transformer's turn ratio without increasing noise. Other signal processing electronic components can be coupled directly to the ends of the probe 120, if desired.

Extending from the preamplifier 130 are electrical wires 132, as shown in FIG. 1, which connect the probe 120 to the electronic processing system for processing the data generated by the probe 120. The wires 132 can be secured to the user's finger and wrist with elastic bands 140 and 142, respectively. The wires 132 can also be secured together to a common substrate to facilitate handling of the inspection apparatus.

The probe 120 is manipulated by the user's finger, which allows the user to directly control the coupling of the probe to the part under inspection. To secure the probe to the user's finger, a finger cover 110 is provided which fits snugly over the user's finger, as shown in FIGS. 1 and 2. The finger cover 110 may comprise cloth, rubber, nylon, or leather, for example, or any other suitable material.

The open end 112 of the finger cover 110 may include an elastic band 114 which secures the finger cover 110 to the finger. The finger cover provides a surface to which the probe 120 is easily attached, removed or rearranged. As shown in FIG. 1, the probe 120 may be attached to the finger cover 110 with a removable attachment means 116 such as Velcro or a hook and loop fastener, or with a suitable adhesive, or thread, for example. Additional attachment means may be provided to secure any additional electronics, such as a preamplifier, transformer, or signal processing components, to the finger cover 110.

The material of the finger cover and the attachment means may be selected to be compatible with any desired inspection conditions. For example, the materials can be selected to be flexible, electrically insulative, thermally insulative, and to absorb vibrations of the part. The finger cover 110 also places the finger at a distance away from the sensor, which minimizes the effect of the capacitance of the human body on the sensor 124.

Because the probe is secured directly to the user's finger, the inspection apparatus provides direct control over the placement of the sensors on the part under inspection and allows the user to make measurements quickly and easily. In addition, the inspection apparatus is small, which allows the user to inspect surfaces which are inaccessible to larger hand-held or machine-controlled probes. The exemplary inspection apparatus also provides the advantage that the user's finger acts as a damping mechanism for acoustic and fractional vibrations in the part.

Another advantage of the inspection apparatus 100 is that it allows the user to couple the interactions between the sensor or sensors and the part very effectively. The probe is flexible, which accommodates a wide range of inspection conditions such as surface curvatures, surface roughness, corrosion, and fasteners. In addition, the probe is directly fixed to the user's finger pads, so that the user can feel the pressure with which the inspection apparatus 100 is applied to the part. The user has direct sensory feedback with respect to the pressure and conformance of the sensor to the part being inspected, which allows the user to instinctively and precisely control the coupling of the sensor to the part. The sensitivity of the inspection apparatus is therefore excellent, since the user can easily provide uniform coupling at various inspection sites on a part.

To facilitate the inspection process, the inspection apparatus 100 can be adapted to arrange the sensor or sensors in any desired position and orientation with respect to the user's finger. This may be accomplished by changing the placement of the probe 120 with respect to the finger cover 110 using the removable attachment means 116. The probe 120 can also be formed such that the sensor 124 is aligned at a desired orientation with respect to the probe 120. This adaptability facilitates the inspection process, because it allows the eddy current sense coil 126 to be oriented in any preferred orientation with respect to the user's finger. For example, if cracks in a part are usually aligned horizontally, it is generally desirable to align the eddy current sense coil to have a substantial vertical component. In this way, the crack disrupts the eddy current effects detected by one sub-coil (e.g. 127) substantially while the eddy current effects detected by the other sub-coil (128) are unaffected, thus producing a large differential signal. The removable attachment mechanism 116 allows the probe and sensor to be easily oriented and reoriented for desired applications.

Figure 3A:
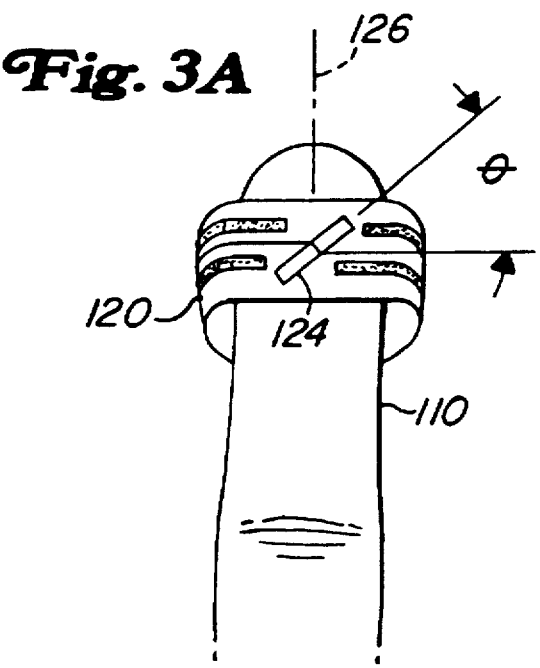
FIGS. 3a–3c show an eddy current probe in various positions and orientations with respect to a user's finger.
Figure 3B:
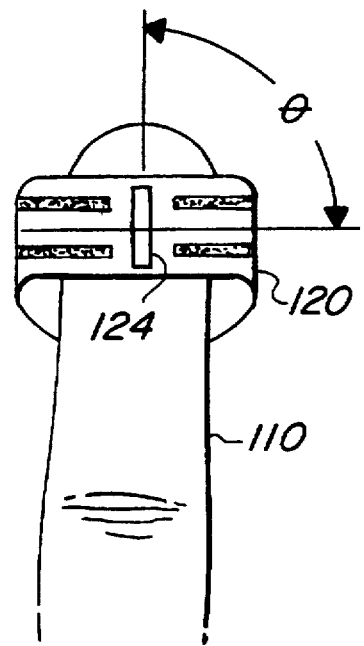
Figure 3C:
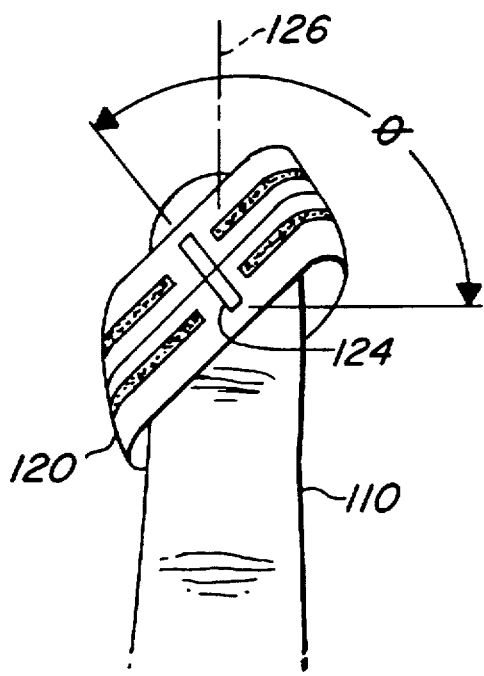

FIGS. 3a–3c illustrate three exemplary configurations of the sensor 124, probe 120, and finger cover 110. In FIGS. 3a and 3b, the probe is arranged perpendicularly to a longitudinal axis 126 of the user's finger. In FIG. 3c, the probe 120 is oblique to the longitudinal axis 126 of the finger. In FIGS. 3b and 3c, the sensor 124 is arranged perpendicularly to a longitudinal axis of the probe 120. In FIG. 3a, the sensor 124 is oblique to a longitudinal axis of the probe 120. FIGS. 1 and 2 show the probe arranged along the length of the finger.

Figure 4:
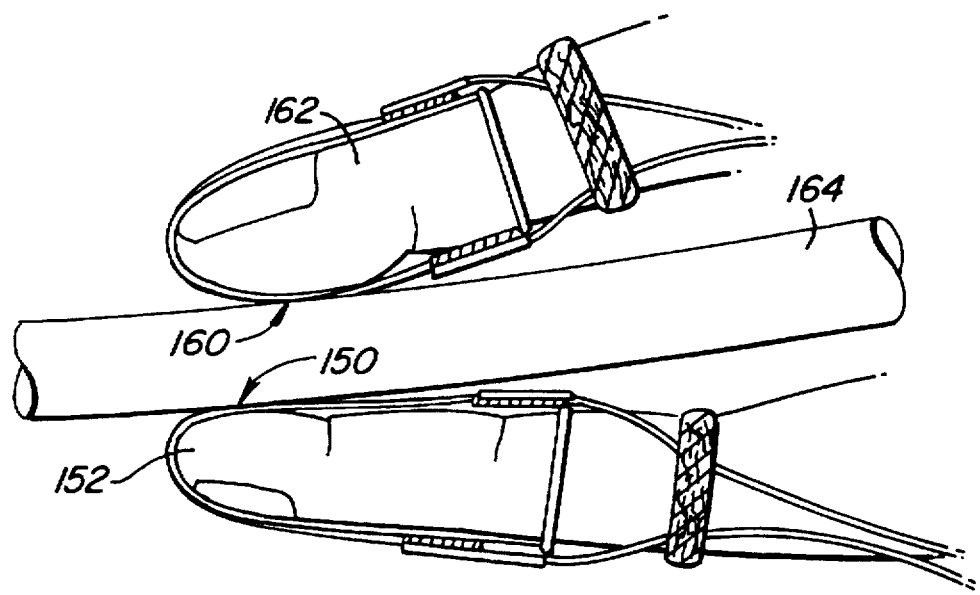
FIG. 4 illustrates the use of multiple probes on multiple fingers.

In some inspection applications, it may be advantageous to attach more than one sensor to a finger, or to attach sensors to more than one finger. The selection of the appropriate sensors depends on the desired application, and may involve different sensing modalities for each finger. For example, a first finger may be equipped with a differential eddy current coil to detect cracks, a second finger may be equipped with an absolute eddy current coil or ultrasonic transducer adapted to measure part thickness, and the user's thumb may be equipped with an ultrasonic transducer for volumetric inspection of the part. FIG. 4 illustrates an example of a probe arrangement in which a first sensor 150 is secured to the user's index finger 152 and a second sensor 160 is secured to the user's thumb 162. Due to the user's direct sensory feedback, the user can quickly and accurately take measurements at inspection points along the tube 164.

An example of a multichannel inspection system 200 coupled to the probe 120 is shown in FIG. 6. Each measurement by the probe 120 is multiplexed by a multiplexer 202 to a collector 204 and separated into independent parallel data channels (CH1, CH2, . . . . CHN). Discrete measurement signals are independently collected and inputted to a demodulating synchronous detector 206 to obtain demodulated signals. The signals are formatted for digital processing by an analog-to-digital converter 208. The digitized signals are then stored in a memory 210.

A processor 212 processes the digitized signals to generate an output signal representative of the measured signals. For example, the processor 212 may generate a visual or audio output signal in real time representative of the magnitude of the differential signal from the differential eddy current sense coil 126. Thus, as the user scans the probe 120 over a part, the magnitude of the differential signal is displayed on the display 214 or represented by audio so that the user can precisely identify the location of a crack on the part in real time. The processor 212 can of course be adapted to process the data in any other desired manner, for example by generating an image of the part displayed on the display 214, showing surface and volume defects of the part.

Figure 8:
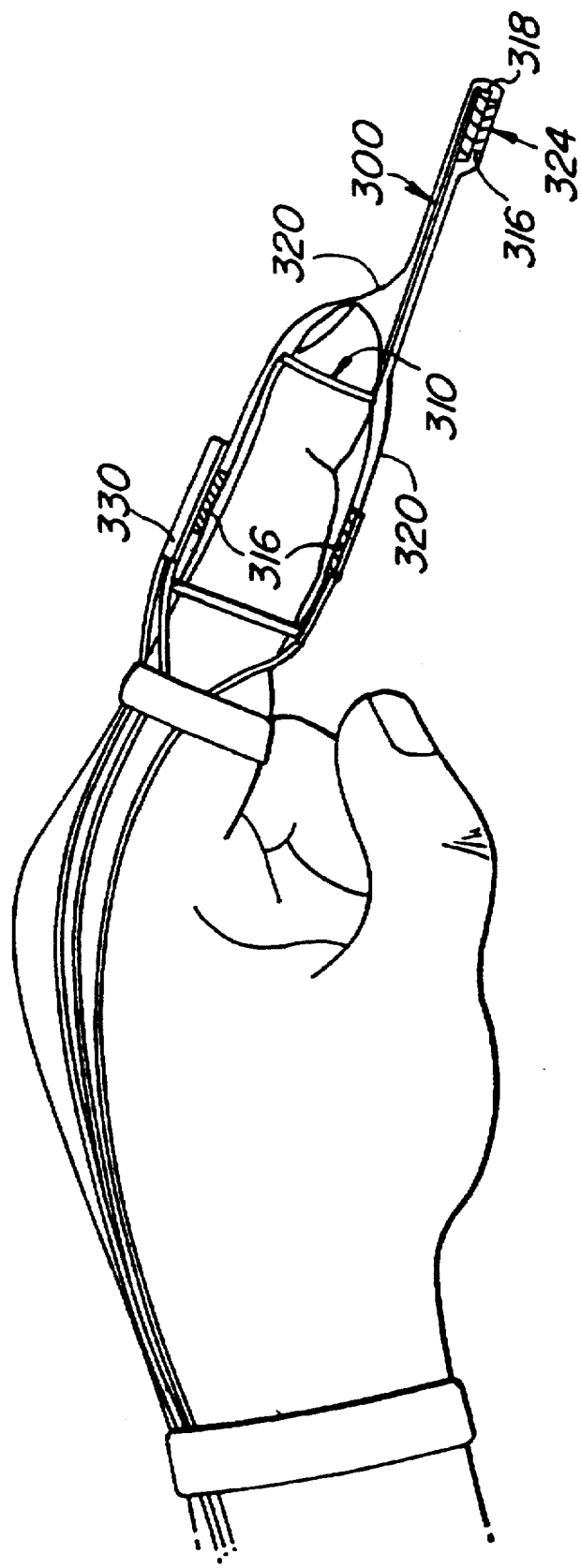
FIG. 8 is an inspection apparatus which includes an extension member according to another embodiment of the invention.

According to another embodiment of the invention, as shown in FIG. 8, the inspection apparatus includes an extension member 300 which is secured between the finger cover 310 and the user's finger. The extension member 300 may comprise a rigid material such as wood or plastic, for example. Fixed to the end of the extension member 300 is a conformable pad 318 which may comprise foam or an encapsulated liquid, for example. The conformable pad 318 absorbs vibrations of the part under inspection and allows the flexible sensor 324 and probe 320 to conform to the part. The probe 320, which houses the flexible sensor 324, is secured with a removable attachment mechanism 316 such as Velcro to the conformable pad 318 at the end of the extension member 300. The probe 320 is also secured to the finger cover 310 with the removable attachment mechanism 316. A preamplifier 330 and other components can be coupled to the probe 320 to reduce the signal to noise ratio of the inspection apparatus, if desired. The extension member 300 is useful for inspecting remote surfaces which are inaccessible even to the user's finger. The extension member 300 may take any form which facilitates access to a desired remote inspection site.

The invention has been described with reference to exemplary embodiments. However, it will be appreciated that various modifications may be made by a person skilled in the art without departing from the scope and spirit of the invention.

What is claimed is:

1. An inspection apparatus for inspecting an article having a surface, comprising:

a flexible sensor conformable to the surface of the article for sensing a characteristic thereof, wherein the flexible sensor comprises an eddy current sensor;

a finger cover which fits over a finger of a user; and attachment means for attaching the flexible sensor to the finger cover.

2. The inspection apparatus of claim 1, wherein the flexible sensor is fixed to a probe comprising a polymer firm.

3. The inspection apparatus of claim 2, wherein the polymer film comprises a plurality of polyimide layers.

4. The inspection apparatus of claim 1, wherein the eddy current sensor comprises an eddy current coil.

5. The inspection apparatus of claim 4, wherein the flexible sensor further comprises an ultrasonic transducer.

6. The inspection apparatus of claim 1, further comprising a second flexible sensor and a second attachment means for attaching the second flexible sensor to the finger cover.

7. The inspection apparatus of claim 1, further comprising a second flexible sensor, a second finger cover, and a second attachment means for attaching the second flexible sensor to the second finger cover, wherein the second finger cover is adapted to fit over a second finger of the user.

8. The inspection apparatus of claim 1, wherein the attachment means allows the flexible sensor to be removably attached to the finger cover and allows an orientation of the flexible sensor with respect to the finger cover to be changed.

9. The inspection apparatus of claim 1, further comprising:

a preamplifier connected to the flexible sensor; and a second attachment means for attaching the preamplifier to the finger cover.

10. The inspection apparatus of claim 1, further comprising a transformer coupled to the flexible sensor; and a second attachment means for attaching the transformer to the finger cover.

11. The inspection apparatus of claim 1, wherein the attachment means provides electrical insulation between the flexible sensor and the user's finger.

12. The inspection apparatus of claim 1, further comprising an extension member which is secured to the user's finger and to the flexible sensor.

13. A method of inspecting an object, comprising the steps of:

attaching a sensor to a finger of a user;

manually applying pressure to the sensor to control conformance of the sensor to a surface of the object;

generating a first signal in the object by inducing an eddy current in the object with the sensor; and receiving a second signal in the sensor representative of a characteristic of the object.

14. The method of claim 13, further comprising the step of changing an orientation of the sensor with respect to the finger of the user.

* * * * *